United States Patent [19]

Solomons et al.

[11] Plant 4,347

[45] Dec. 12, 1978

[54] **NON-TOXIC STRAIN OF *FUSARIUM GRAMINEARUM***

[75] Inventors: Gerald L. Solomons, High Wycombe; Gerald W. Scammell, Chinnor, both of England

[73] Assignee: Ranks Hovis McDougall Limited, London, England

[21] Appl. No.: 642,610

[22] Filed: Dec. 19, 1975

Related U.S. Application Data

[63] Continuation of Ser. No. 417,190, Jan. 7, 1974, abandoned, which is a continuation of Ser. No. 140,303, May 4, 1971, abandoned.

[30] Foreign Application Priority Data

May 14, 1970 [GB] United Kingdom ..... 23452/70

Jun. 24, 1970 [GB] United Kingdom ..... 30584/70

[51] Int. Cl.[2] ..... A01H 15/00

[52] U.S. Cl. ..... Plt./89

[58] Field of Search ..... 47/58; Plt./89

[56] References Cited

FOREIGN PATENT DOCUMENTS 767231 10/1971 Belgium ..... 47/58

*Primary Examiner*—Robert E. Bagwill

*Attorney, Agent, or Firm*—Stevens, Davis, Miller & Mosher

[57] ABSTRACT

A non-toxic, edible strain of *Fusarium graminearum* fungus. The fungal mycelium is a nutritious material having a high net protein utilization value.

6 Drawing Figures

This application is a continuation application of application Ser. No. 417,190, filed Jan. 7, 1974, now abandoned, which in turn is a continuation application of our earlier filed co-pending application Ser. No. 140,303 filed May 4, 1971 now abandoned.

The present invention relates to a new and distinct non-toxic strain of fungi of the genus Fusarium and especially to strain of *Fusarium graminearum.*

The non-toxic strain is our strain of *Fusarium graminearum* Schwabe, deposited with the Commonwealth Mycological Institute and assigned the number I.M.I. 145425. The strain has also been deposited with the American Type Culture Collection, 12301 Parklawn Drive, Rockville, Md. 20852, where it has been assigned the number ATCC No. 20334.

Our new strain of *Fusarium graminearum* Schwabe, I.M.I. 145425, is non-pathogenic to wheat. It has the following morpholigical characteristics:

| Media | Potato Sucrose Agar | Czapek-Dox (Modified) Agar (Oxoid) |
|---|---|---|
| | 250 grams of potatoes washed and diced, placed in pressure cooker 15 lbs. square inch for 15 minutes. The decoction is then squeezed through two layers of muslin. 2% of Glucose & 2% of Agar are added to the turbid filtrate and the medium autoclaved and dispersed. | |
| Growth conditions | 25° C several weeks | |
| Rate of growth: | 4.0 cm. in 3 days | 3.0 cm. in 3 days |

Character of growth: Floccose, spreading colonies with white aerial mycelium. Subtratum on PSA greyish rose with patches of crimson to yellow. Tendency to be somewhat paler on CDA. Occasionally deep red pigment produced, particularly on aging. After one to two weeks the aerial mycelium tends to become brown and collapse. The colony then becomes rather slimy as sporodochia are formed the color being pink to brown on PSA and salmon pink on CDA.

No exudate is formed and pigment formation tends to follow the mycelium color.

Conidia: Microconidia not produced by this organism. Macroconidia produced from single lateral phialides or multibranched conidiophores with short phialides. In older cultures the conidiophores aggregate to form sporodochia, particularly on CDA. The conidia vary from falcate to curved fusoid dorsi-ventral, septation varying from 3 to 5, commonly 5 in younger cultures. Spore size varies from 25–50$\mu \times$ 2.5–4.0$\mu$.

The foot cell is often pedicellate, particularly in the longer 5 septate spores. Swollen cells occur in the mycelium and occasionally chlamydospores occur intercalary, singly or in chains.

This strain was isolated from a soil sample taken from a highly cultivated garden in Marlow, Buckinghamshire, England. It has been reproduced by conventional microbiological means including transferring both macro-conidia (one of its reproductive systems) and its mycelia (which is a vegetative propagation).

Figure 3:
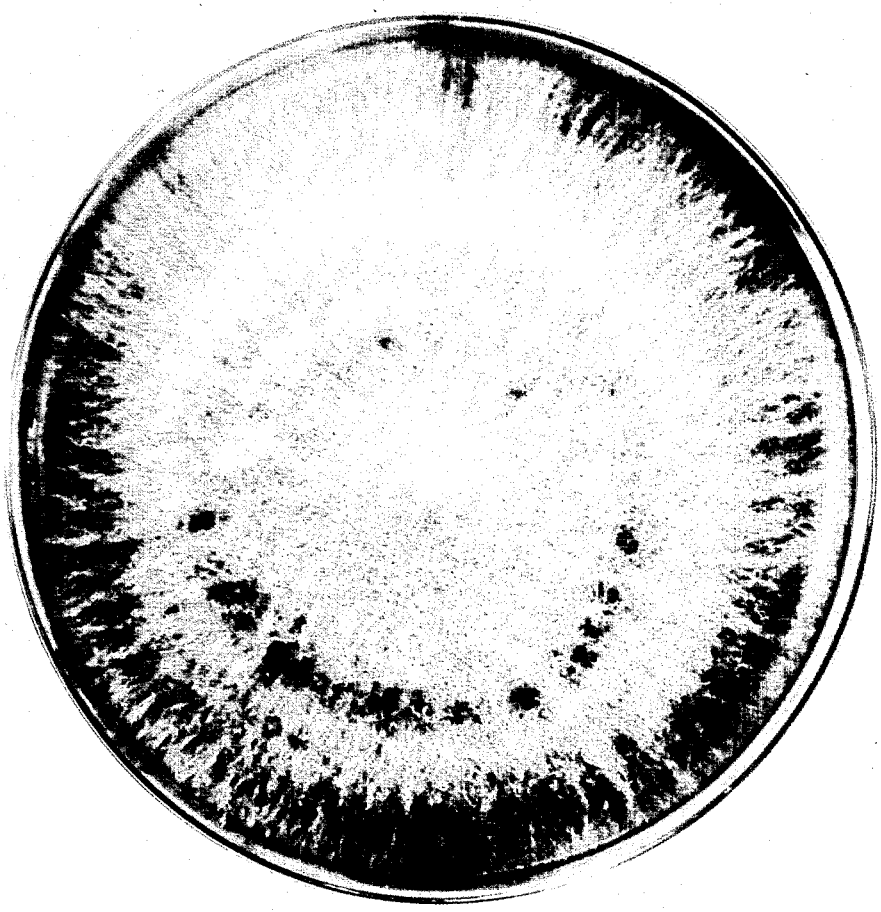

FIG. 3 illustrates a colony of *Fusarium graminearum* IMI 145425 grown on Malt Extract medium (Oxoid) in a petri-dish at 30° C for 8 days. This demonstrates the white aeriel floccose mycelium in the younger (outer) part of the culture. The older mycelium has collapsed and is slightly brown. (1½ $\times$ natural size) (Oxoid is a trademark).

Figure 1:
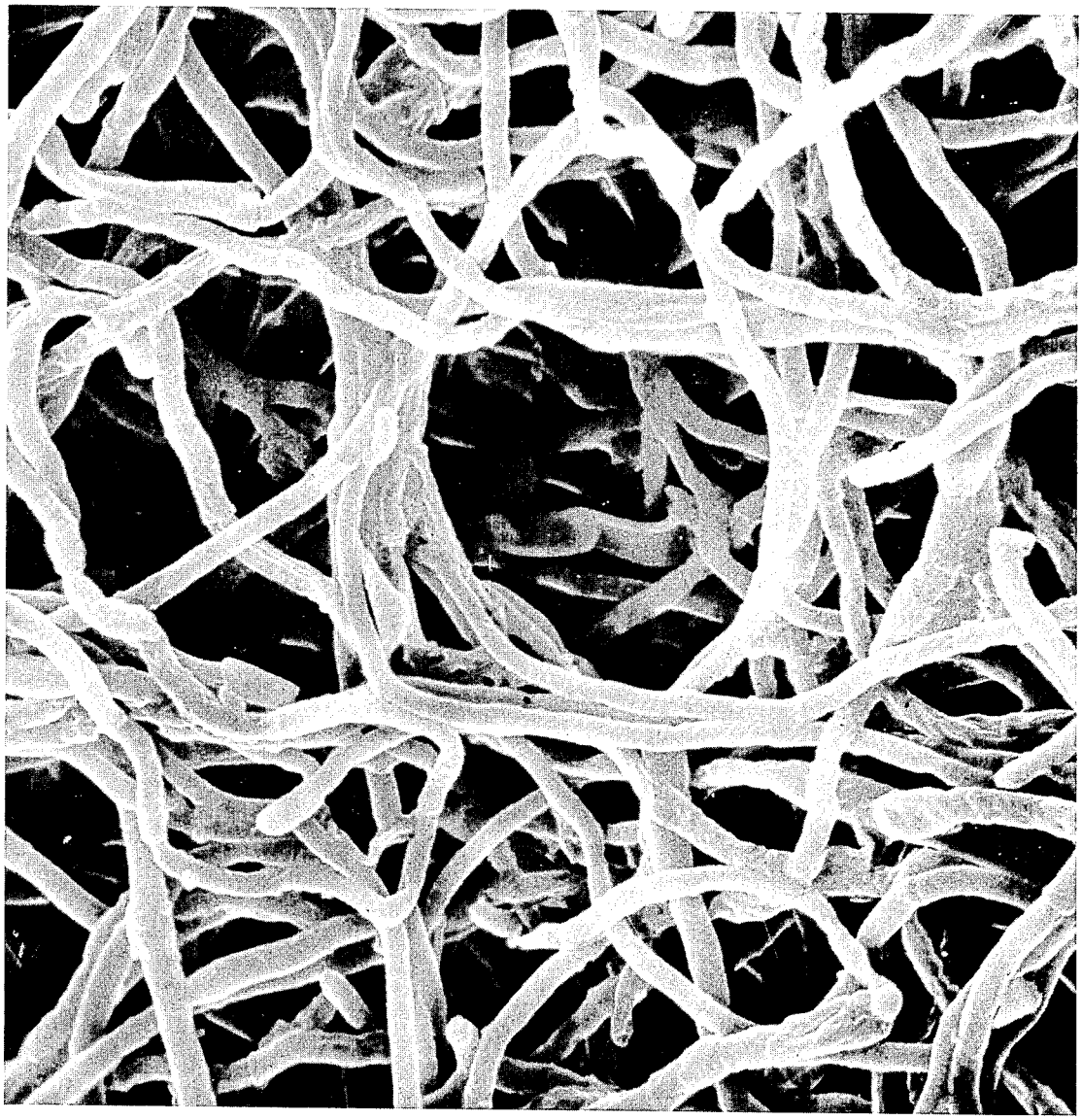
FIG. 1 is a "stereoscan" micrograph of the fungal hyphae.
Figure 2:
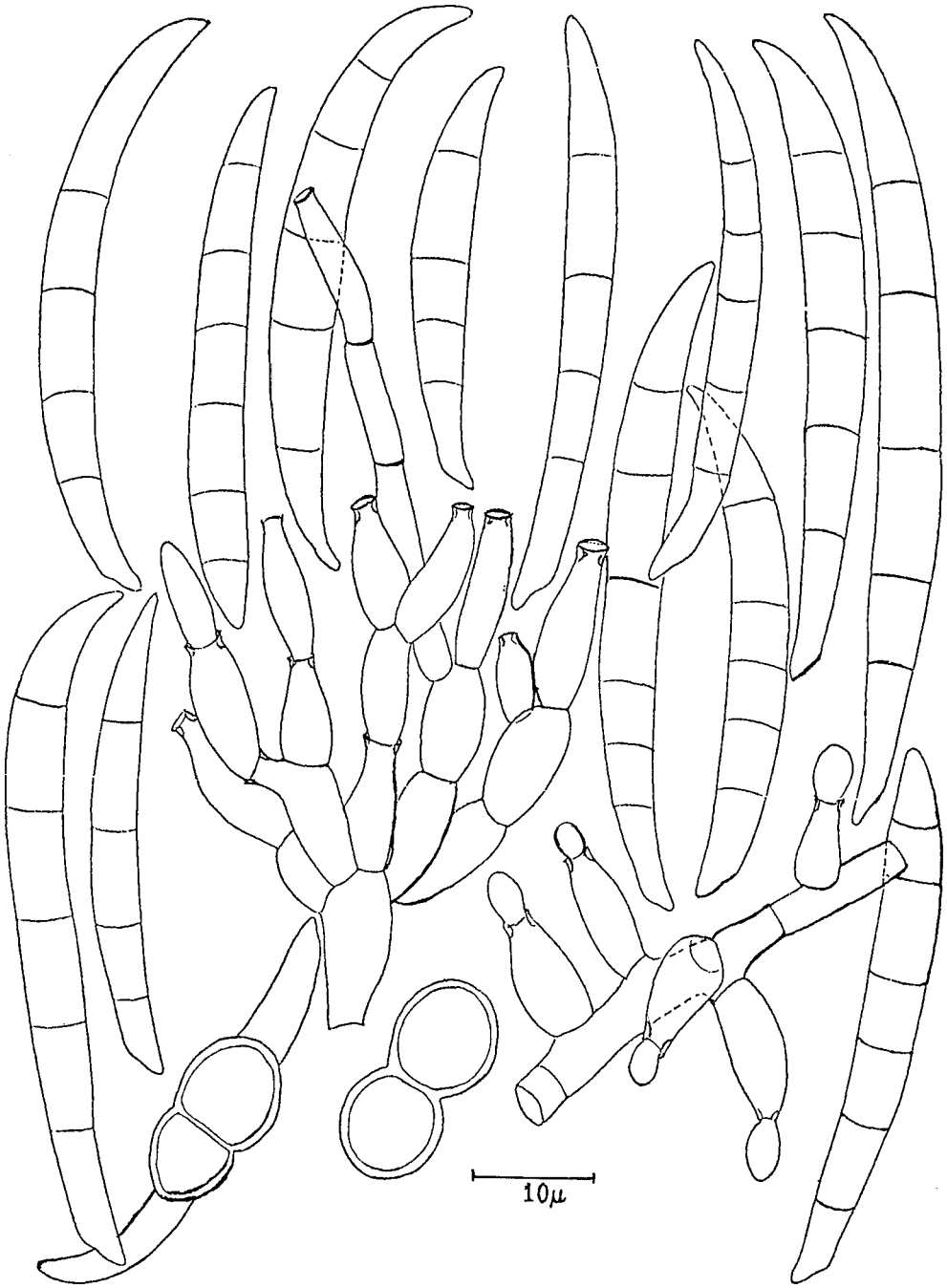
FIG. 2 illustrates the macroconidia and chlamydospore characteristics of the *Fusarium graminearum.*
Figure 4:
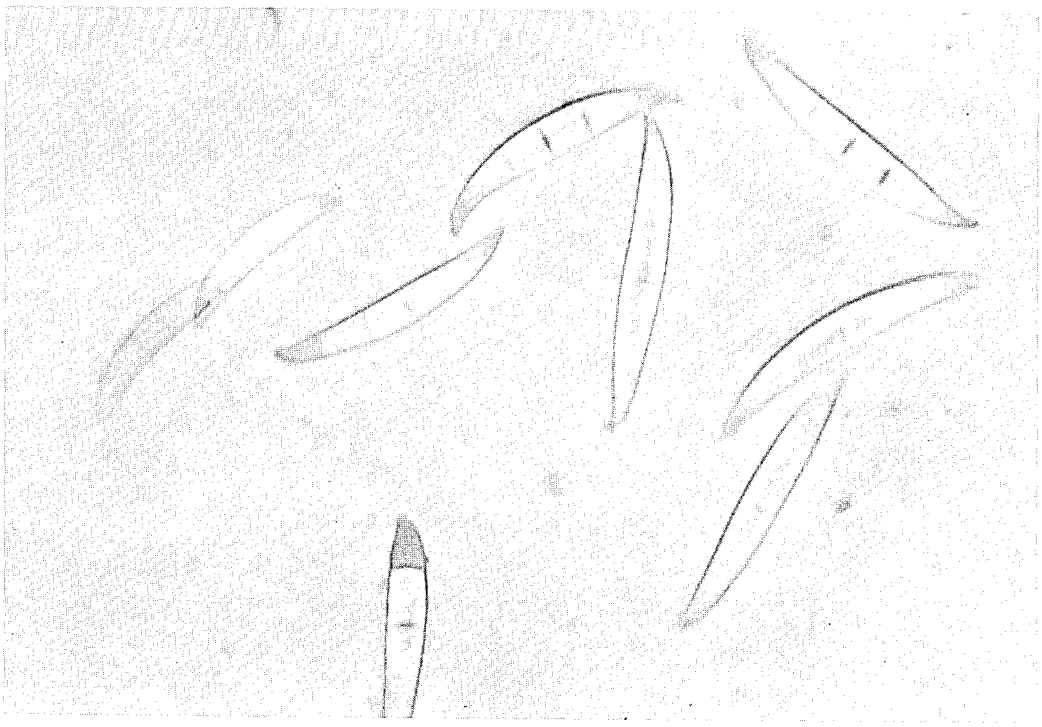
Figure 6:
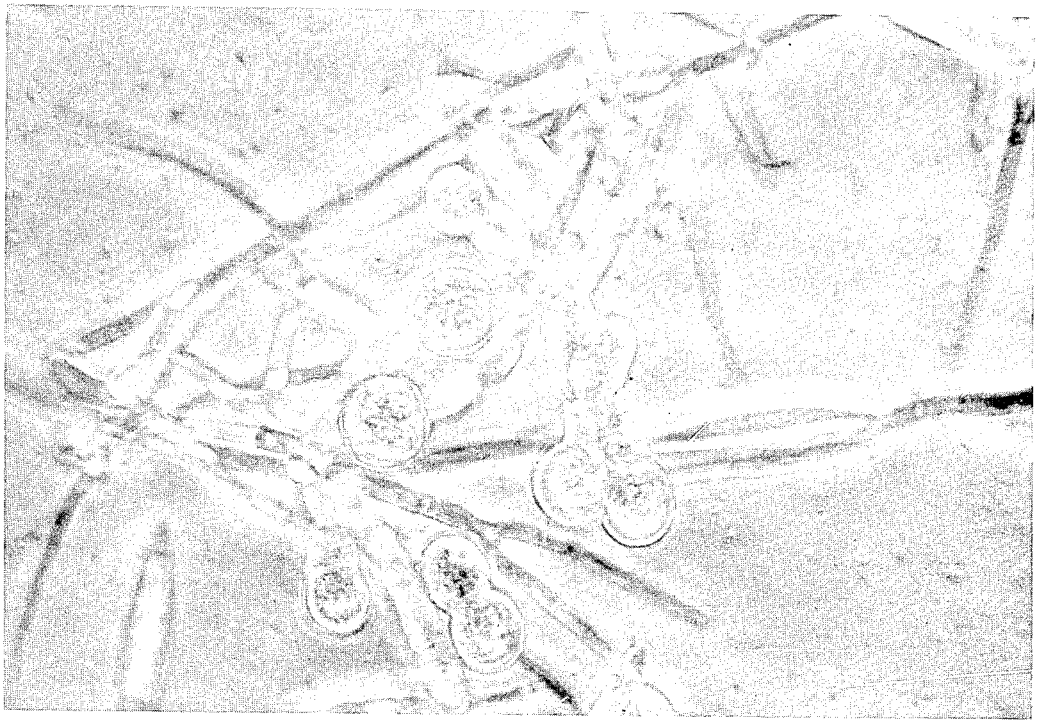
Figure 5:
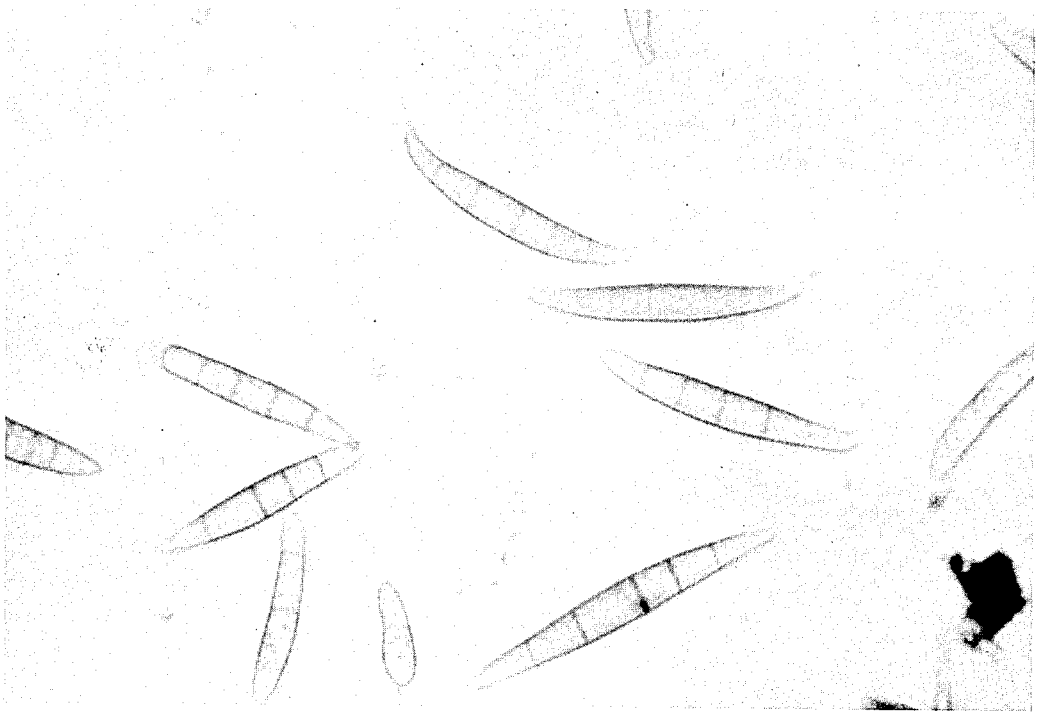

FIGS. 4–6 illustrate microscopic preparations from colony similar to above, mounted in 2.5% Glutaraldehyde in 0.1M Sodium cacodylate and 0.01M Calcium chloride and photographed under phase contrast illumination. (Final magnification $\times$ 1000).

Specifically, FIGS. 4 and 5 illustrate Macroconidia, demonstrating varying degree of septation. Five cell macroconidium demonstrates pedicellate foot cell and curved fusiform shape.

FIG. 6 illustrates Chlamydospores, terminal and intercalary, being produced in older mycelium.

The present strain is distinguished from other strains of *Fusarium graminearum* by a three stage examination process as follows:

Stage I — Colony and Morphological Characteristics

Examine, on various agars, the colony formation and rate of growth, paying special attention to the shape of the macroconidia and the number of segments within the macroconidia.

Stage II

Examine the growth and characteristics in submerged culture on defined culture medium and examine strains for the production of toxins, e.g. Zearalenone and Tricothecenes. Also examine the strains for plant pathogenicity.

These two stages would eliminate the vast majority of other strains of *Fusarium graminearum.*

Stage III — DNA Hybridization Techniques

In this, the genetic information stored in the DNA of the organism would be hybridized with the DNA of the unknown strains and checked for irregularities.

This strain may be used to provide an edible protein-containing fungal mycelium which possesses a high net protein utilization value on rat assays of at least 70 based on the α-amino nitrogen by incubating and proliferating, under aerobic conditions, the non-toxic strain of genus Fusarium in a culture medium containing essential growth-promoting nutrient substances, of which carbon in the form of assimilable carbohydrate constitutes the limiting substrate in proliferation, and separating the proliferated organism comprising the edible protein-containing substance.

The separated proliferated organism comprising the edible protein-containing substance may be incorporated into a foodstuff for human or animal consumption.

The substrate employed in the incubation stage may be of vegetable origin, for example starch, starch-containing materials or products of their hydrolysis, sucrose, sucrose-containing materials or hydrolyzed sucrose, i.e. invert sugar or mixtures thereof. Thus the substrate may comprise hydrolyzed potato, molasses, glucose, hydrolyzed bean starch or cassava. Alternatively substrate of animal origin comprising whey may be employed.

The temperature of incubation is in general between 25° and 34° C and preferably around 30° C.

Inoculation resulting in commencement of the process is best carried out by a pregerminated seed stage comprising, for example, from 2% to 10% of inoculum, usually in the range 5% to 10%.

The pH of the substrate medium during incubation is preferably kept within a suitable range supporting maximum growth, for example, between 3.5 to 7.

The period of growth in batch culture under the above-mentioned conditions is usually found to range from 20 to 48 hours. In both batch and continuous processes aeration and agitation should be carried out to provide a sufficient level of dissolved oxygen to overcome deficiency which can be a limiting growth factor.

As will be well understood by those skilled in the art sufficient quantities of essential growth nutrients such as nitrogen, sulphur, phosphorus and other trace elements are maintained in the substrate medium so that growth of the substance is limited only by the carbohydrate available to the fungus.

In addition to the nutrients stated above the presence of one or more vitamins such, for example, as biotin may be desirable to maintain maximum growth rate.

It is also desirable to add a non-toxic anti-foaming agent to the substrate medium to control foaming during the fermentation.

The substance produced may be isolated in any suitable manner known in the art. Thus the resulting mycelium may be recovered by separation, washing, filtration and drying. In this connection, however, it has been found that if the moisture content of the substance is reduced below a critical level of about 50% (w/w) by filtration under pressure the subsequent drying methods employed are not subjected to such stringent temperature limitations which is an important factor in the economic processing of these materials. The method of drying must not cause damage to the nutritional value of the mycelium and may be drying in a current of air at 75° C or freeze drying.

The fungal mycelium produced from the present novel strain shows very good water binding capacity and may be useful as a thickening and gelling agent. Not being an isolate, it retains its vitamins as well as other nutritionally available materials such as lipids and some carbohydrates. Fungal mycelium has satisfactory baking characteristics which are of value in protein enriched breads, breakfast foods and food snacks. The fungal mycelium, because of its filamentous structure, can be baked, fried or puffed and presented to many communities as a food comparable in appearance and acceptability with conventional foods which they are accustomed to eating.

Following is a description by way of example of methods of cultivating the novel strain to obtain the mycelium product.

Examples 1–4 are of batch culture.

EXAMPLE 1

10 Liters of the following culture medium were prepared and sterilized as described in a stirred fermenter vessel.

| | |
|---|---|
| Cane molasses to provide | 6% w/v sugar |
| Ammonium sulphate | 1.2% |
| $NaH_2PO_4$ | 0.25% |
| Sterilized 30 minutes | 15 psig |
| $CaCO_3$ | 0.5% w/v |
| Sterilized 3 hours | 15 psig |

The medium components were added aseptically and attemperated to 30° C. An inoculum equivalent to 5–10% by volume of the culture medium and grown either on a glucose/corn steep liquor medium or other suitable materials in shake flasks was inoculated with a spore suspension of the organism comprising our strain of *Fusarium graminearum* Schwabe I.M.I. 145425, and grown for 18–24 hours at 30° C on a rotary shaker, and added aseptically to the fermenter.

The fermenter incubated at 30° C was then stirred at 800 rpm with a 6-bladed disc turbine (0.5D) in a full baffled vessel and 1 VVM of sterile air passed through. After 35 hours, the grown mycelium was removed from the fermenter, centrifuged, washed with water and dried in a warm air band drier, air temperature 75° C.

The dried product had the following composition:

| | | |
|---|---|---|
| Total Nitrogen | 8.0% | |
| Ash | 5.3% | |
| Lipid | 2.7% | |
| NPUop. | 52 | based on Total Nitrogen |

EXAMPLE 2

10 Liters of the following culture medium were prepared and sterilized as described in a 14 liter New Brunswick, Microferm fermenter.

| | | | Final % |
|---|---|---|---|
| Solution 1 | Glucose | pH 3.0 | 3.0 |
| Solution 2 | Ammonium sulphate | | 0.7 |
| Solution 3 | Potassium di-hydrogen phosphate | pH 5.0 | 1.0 |
| Solution 4 | $FeSO_4\ 7H_2O$ | pH 2.5 | 0.001 |
| | $MnSO_4\ 4H_2O$ | | 0.0005 |
| | $CuSO_4\ 5H_2O$ | | 0.0001 |
| | $MgSO_4\ 7H_2O$ | | 0.025 |
| Solution 5 | $Na_2MoO_4\ 2H_2O$ | | 0.0001 |
| | $CoCl_2\ 6H_2O$ | | 0.0001 |
| | $CaCl_2\ 2H_2O$ | | 0.0015 |
| Solution 6 | NaOH | | 0.1 |

All the above solutions were sterilized by heat for 15 minutes at 15 psig.

Solution 7 Vitamins and/or amino acids as described below sterilized by filtration.

The solutions were added aseptically to the vessel.

An inoculum was grown and added as in Example 1 except that the final concentration in the fermenter was adjusted so as to provide 0.5 gm/l dry wt. of mycelium.

The conditions of growth were temperature 30° C; aeration 1 VVM, stirrer speed was adjusted to maintain a level of dissolved oxygen above 25% of the saturation value in the culture medium, measured by a New Brunswick Inc. DO probe. Sterile anti-foam, polypropylene glycol 2000, was added as required to suppress foam and pH was maintained between 6.0–6.3 by the addition of sterile potassium hydroxide solution.

| | | Growth rates ($hr.^{-1}$) |
|---|---|---|
| (i) | Omitting solution 7 (Minimal medium) | very slow |
| (ii) | Solution 7 such that the final concentration of Biotin in the culture medium was 50μg/l | 0.2 |
| (iii) | Solution 7 such that the final concentration of Biotin in the culture medium was 50 μg/l; Choline chloride 30 mg/l and Methionine 300 mg/l | 0.25 |

EXAMPLE 3

Medium and conditions were as in Example 2, but the glucose was replaced with maltose.

| | | |
|---|---|---|
| (i) | Solution 7 as Example 2 (ii) | 0.18 |
| (ii) | Solution 7 as Example 2 (iii) | 0.21 |

EXAMPLE 4

100 Liters of the following culture medium were prepared and sterilized as described in a 130 l. stainless steel fermenter.

| | % final concentration |
|---|---|
| Glucose | 4.0 |
| Corn steep liquor (50% Total Solids) | 0.8 |
| Ammonium sulphate | 0.2 |
| Potassium di-hydrogen phosphate | 0.2 |
| $MgSO_4\ 7H_2O$ | 0.025 |
| $ZnSO_4\ 7H_2O$ | 0.0005 |
| $FeSO_4\ 7H_2O$ | 0.0005 |
| $MnSO_4\ 4H_2O$ | 0.0001 |

The medium was sterilized at pH 3.0 at 15 psig for 30 minutes and on cooling to 30° C adjusted to pH 5.0 by the sterile addition of ammonia.

Biotin sterilized by filtration to give 40μg/l final concentration was added aseptically.

The vessel was inoculated with 10 liters of culture grown in a sparged vessel, for 18 hours, at 30° C, on a medium containing: Glucose 2%; tryptone (oxoid) 0.4%; yeast extract (oxoid) 0.1%; ammonium sulphate 0.15%; potassium di-hydrogen phosphate 1%; sodium hydroxide 0.1%; magnesium sulphate 0.025%; ferrous sulphate 0.001%; zinc sulphate 0.001%; manganese sulphate 0.0005%; copper sulphate 0.001%; anti-foam, polypropylene glycol 2000 0.5% and sterilized for 45 minutes at 15 psig, inoculated with a spore suspension of our organism *Fusarium graminearum* Schwabe I.M.I. 145425.

The conditions for growth were temperature 30° C, aeration adjusted to provide dissolved oxygen concentrations above 10% of the saturation value for the culture broth. Sterile anti-foam, polypropylene glycol 2000, was added to suppress foaming and the pH was maintained at 5.0 by means of sterile ammonia additions. Samples of the mycelium taken over the period of growth contained, on a dry weight basis: Total Nitrogen 8.0–8.6%; α-Amino nitrogen 6.4–6.6%. The initial growth rate in this complex medium derived from both the batched culture medium and inoculum was approximately 0.3 $hr.^{-1}$.

The following Examples 5 and 6 are of continuous culture.

EXAMPLE 5

Culture medium of the following composition was prepared:

| Solution 1 | Final % |
|---|---|
| Glucose | 3.0 |
| Ammonium sulphate | 0.25 |
| Potassium di-hydrogen phosphate | 0.3 |
| Magnesium sulphate | 0.025 |
| Anti-foam, polypropylene glycol 2000 | 0.01 |
| Sterilized at pH 3.0 for 30 minutes at 15 psig | |
| Solution 2 | |
| $MnSO_4\ 4H_2O$ | 0.0005 |
| $FeSO_4\ 7H_2O$ | 0.0005 |
| $ZnSO_4\ 7H_2O$ | 0.0005 |
| $CoCl_2\ 6H_2O$ | 0.0001 |
| $CuSO_4\ 5H_2O$ | 0.0001 |
| $Na_2MoO_4 2H_2O$ | 0.0001 |
| Sterilized 15 minutes at 156 psig | |

Solution 3

Vitamins and/or amino acid as described below sterilized by filtration.

All solutions were added as necessary, aseptically. In 8.5 liter chemostat the conditions of growth were as follows:

Temperature 30° C; aeration 1 VVM; agitation 800 rpm single 6-bladed disc turbine 0.5 D in fully baffled vessel. Organism, our strain of *Fusarium graminearum* Schwabe I.M.I. 145425. The pH maintained at 5.0 by automatic addition of sterile ammonia.

| | | μMax. hr.$^{-1}$ | Yield factor | Mycelium TN% | Mycelium AN% | NPU based onTN | NPU based onAn |
|---|---|---|---|---|---|---|---|
| (i) | Solution 3 such that the final concentrate of Biotin in the culture medium was 20 μg/1 | 0.17–0.19 | 0.5 | 7.2 to 7.9 | 6.3 to 6.8 | 54 | 65 |
| (ii) | Solution 3 such that the final concentrate of Biotin in the culture medium was 20 μg/1 and of methionine was 600 μg/1 | 0.20–0.21 | 0.5 | 7.7 to 8.6 | 6.1 to 6.5 | 59 | 78 |

EXAMPLE 6

Culture medium of the following composition was prepared:

| | % |
|---|---|
| Bean starch (α-amylase treated) | 3.0 carbohydrate |
| Corn steep liquor | 1.33 |
| Ammonium sulphate | 0.25 |
| Potassium di-hydrogen phosphate | 0.15 |
| Magnesium sulphate | 0.025 |
| Antifoam polypropylene glycol 2000 (v/w) | 0.025 |

Sterilized pH 4.0 for 30 minutes at 15 p.s.i.g.

The medium was fed to the 8.5 liter chemostat under the same conditions as in Example 5 except that the pH was varied between 3.5 and 6.0 and growth rate throughout 0.1 hr$^{-1}$. The following result was obtained:

| | TN % | AN % | NPU based on TN | NPU based on AN |
|---|---|---|---|---|
| Product grown at pH 4.0 | 7.8 | 6.6 | 54 | 67 |
| Product grown at pH 5.0 | 8.6 | 7.1 | 57 | 71 |
| Product grown at pH 6.0 | 7.7 | 5.9 | 61 | 80 |

EXAMPLE 6(b)

The culture medium and conditions were as in Example 6 except that the pH was held at 5.0 throughout the run and the temperature was varied between 26° and 34° C. The optimum temperature was found to be 30°–32° C.

Methods of analysis for Total Nitrogen (TN) Automatic Kjeldahl digester (Technicon). A Ferrari, Ann. N.Y. Sci. 87, 792 (1960).

Amino nitrogen (AN) TNBS (modified). M. A. Pinnegar, Technicon Symposium 1965, p. 80.

We claim:

1. A novel non-toxic fungi *Fusarium graminearum* as shown and described in the foregoing specification and drawings which has been deposited with the Commonwealth Mycological Institute and identified as *Fusarium graminearum* Schwabe I.M.I. 145425.

* * * * *

UNITED STATES PATENT OFFICE

CERTIFICATE OF CORRECTION

Patent No. P.P. 4347 Dated December 12, 1978

Inventor(s) Gerald R. SOLOMONS et al

It is certified that error appears in the above-identified patent and that said Letters Patent are hereby corrected as shown below:

Column 1, line 8, before "strain" insert -- a --.

Column 1, line 18, change "morpholigical" to -- morphological --.

Column 3, line 33, before "genus" insert -- the --.

Column 6, line 60, change "156 psig" to -- 15 psig --.

Signed and Sealed this

*Sixteenth* Day of *September 1980*

[SEAL]

*Attest:*

SIDNEY A. DIAMOND

*Attesting Officer*

*Commissioner of Patents and Trademarks*